United States Patent [19]

Karami

[11] 4,047,531

[45] Sept. 13, 1977

[54] ABSORBENT ARTICLE WITH DIFFERENTIAL PAD

[75] Inventor: Hamzeh Karami, Crystal Lake, Ill.

[73] Assignee: Colgate-Palmolive Company, New York, N.Y.

[21] Appl. No.: 713,086

[22] Filed: Aug. 9, 1976

[51] Int. Cl.[2] .................. A61F 13/02; A61F 13/16
[52] U.S. Cl. .................. 128/290 R; 128/287
[58] Field of Search ............ 128/287, 290 R, 290 P, 128/290 B

[56] References Cited

U.S. PATENT DOCUMENTS

| 3,105,491 | 10/1963 | Harwood | 128/290 R |
| 3,612,055 | 10/1971 | Mesek et al. | 128/287 |
| 3,636,952 | 1/1972 | George | 128/287 |
| 3,666,611 | 5/1972 | Uoa | 128/290 P |
| 3,867,940 | 2/1975 | Mesek et al. | 128/287 |
| 3,901,238 | 8/1975 | Gellert et al. | 128/287 |
| 3,916,900 | 11/1975 | Breyer et al. | 128/287 |
| 3,971,379 | 7/1976 | Chatterjee | 128/285 |

FOREIGN PATENT DOCUMENTS 828,682  11/1975  Belgium .................. 128/287

OTHER PUBLICATIONS

Pulp & Paper, vol. 1 (1960) "Pulping", pp. 319, 320.
"Mechanical Pulp in Absorbent Qualities", E. Bohmer, ABIPC, vol. 44, No. 7, pp. 698, 699–No7228.
Bohmer, E. "Mechanical Pulp in Absorbent Qualities", Norsk Skogindustri 27, No. 9, pp. 249–252.

Primary Examiner—Aldrich F. Medbery
Attorney, Agent, or Firm—Powell L. Sprunger

[57] ABSTRACT

An absorbent article of a size for placement against a wearer for capturing body fluids comprising, a backing sheet of fluid impervious material, a fluid pervious cover sheet, and an absorbent pad positioned intermediate the backing and cover sheets. The pad has a first layer having a mass of fibers substantially formed from a mechanical, thermomechanical, or semichemical fluff, and a second layer having a mass of fibers substantially formed from a thermomechanical, semichemical, or chemical fluff.

9 Claims, 3 Drawing Figures

ABSORBENT ARTICLE WITH DIFFERENTIAL PAD

BACKGROUND OF THE INVENTION

The present invention relates to absorbent articles.

A various assortment of absorbent articles, such as disposable diapers, have been proposed for use in capturing and retaining body fluids when placed against a wearer. For example, disposable diapers are normally made with a fluid pervious cover sheet, a fluid impervious backing sheet, and an absorbent pad positioned between the cover and backing sheets. Many of such pads are made from wood fluff which is normally formed by fiberizing or comminuting pulp board. The pump board itself is normally formed from trees through a pulping process. The pulping processes may be categorized as chemical, semichemical, mechanical, and thermomechanical.

All of the wood fluff used in absorbent articles sold in the United States known to the applicant has been predominantly formed from a chemically produced pulp. For a given species of wood, the chemical pulping process produces a pulp having fibers with a longer length than the fibers produced by the other pulping processes, particularly the mechanical pulping process. Accordingly, the industry has sought chemically produced pulp for use in disposable pads since the long fibers enhance the structural integrity and loft of the pad.

In spite that the chemical pulp results in a pad with desirable characteristics, a number of disadvantages are inherent in the use of such pulp. First, the chemical pulping process is relatively inefficient in that the yield of pulp to the amount of wood used in pulping is in the range of 40 to 55% whereas the yield of the mechanical, thermomechanical, and semichemical pulping processes is as high as 90–95%. The disparity in yields between the processes is due to the removal of lignin, cellulose, and hemicellulose from the wood during digestion in the chemical procedure. Accordingly, chemically produced pulps are significantly higher in cost than mechanical, thermomechanical, and semichemical pulps, necessarily resulting in a more costly item to the consumer. Also, the vital raw materials are not used to the desired extent in chemical pulps, thus detracting from our natural resources.

Second, environmental considerations favor the use of pulps which are not produced by the chemical process. In the chemical sulfite process, it is relatively difficult to reclaim the cooking chemicals used during pulping. Hence, the manufacturer must dispose of the chemicals, and it is believed that more than one sulfite processing plant has been closed due to contamination of water by the chemicals, which the Environmental Protection Agency considers dangerous. Although it is less difficult to reclaim the chemicals used in chemical kraft pulping, this process is characterized by the emission of gases containing malodorous substances, such as mercaptans and organic sulfides, and is also repugnant to the community at large.

Third, the energy required to fiberize pulp board solely of the chemical type is greater than that necessary for a pulp board containing mechanical or thermomechanical produced pulp. This follows since lignin of the fibers is removed during chemical pulping, thus increasing hydrogen bonding between dry fibers of the chemical pulp.

Finally, it is preferred to obtain an absorbent pad which overcomes the above objections, and yet has superior properties when used in the article. For example, the fibers in pads made solely from chemical pulps are relatively hydrophilic, and collapse when wetted and placed under loads, thus reducing the interfiber spacings in the pad. Thus, although readily absorbent, the fluid holding capacity of the pad becomes reduced where wetted and compressed, and the pad tends to cause backwetting through the cover sheet in this area.

SUMMARY OF THE INVENTION

A principal feature of the present invention is the provision of an absorbent article of significantly reduced cost and having improved fluid receiving and retaining capabilities.

The article of the present invention comprises, a backing sheet of fluid impervious material, a fluid pervious cover sheet, and an absorbent pad positioned intermediate the backing and cover sheets. The pad comprises a first layer having a mass of fibers substantially formed from a mechanical, thermomechanical, or semichemical fluff, and a second layer having a mass of fibers substantially formed from a thermomechanical, semichemical, or chemical fluff. In a preferred form, the second layer is positioned intermediate the first layer and the backing sheet, and the average fibers in the first layer are more hydrophobic relative the average fibers in the second layer.

A feature of the present invention is that the relatively hydrophobic first layer is more resilient than the second layer when wetted and placed under loads, and readily passes body fluids from the cover sheet to the lower second layer.

Another feature of the present invention is that the relatively hydrophilic second layer has interfiber spacings of reduced size when wetted and placed under loads, becomes highly absorbent, and rapidly disperses fluids through the second layer.

Thus, a feature of the present invention is that the body fluids are readily absorbed by the second layer from the first layer, and are transmitted in the lower second layer until saturation thereof.

Another feature of the present invention is that the body fluids are preferentially retained in the lower second layer, thus reducing wetness of the first layer and maintaining the cover sheet against the wearer's body in a relatively dry condition.

Yet another feature of the present invention is that the pad in the article of the present invention may be made at a substantially reduced cost.

Further feature will become more fully apparent in the following description of the embodiments of this invention and from the appended claims.

DESCRIPTION OF THE PREFERRED EMBODIMENTS

Although for convenience the articles of the present invention will be described primarily as disposable diapers, it will be understood that the articles may be of any suitable type, such as sanitary napkins or maternity napkins.

Figure 1:
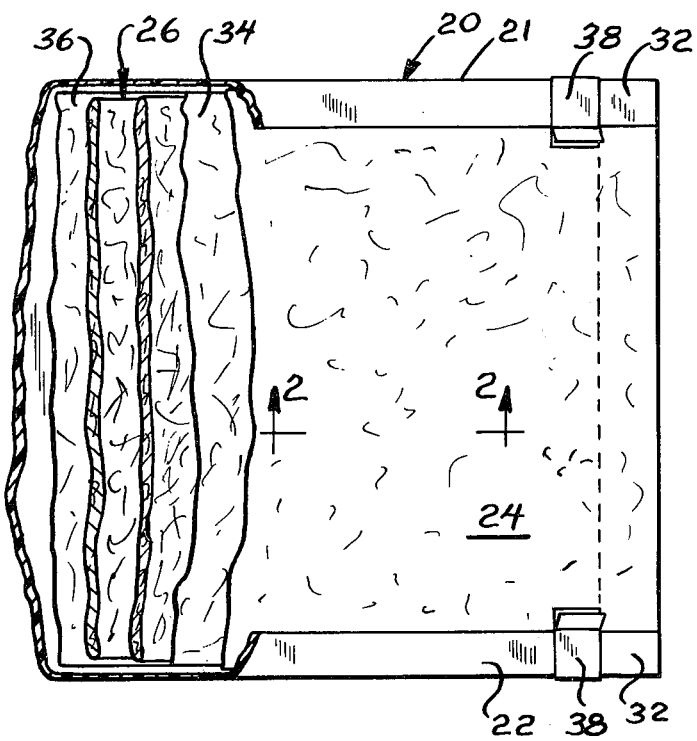
FIG. 1 is a fragmentary plan view of an absorbent article of the present invention being shown as a disposable diaper.
Figure 2:
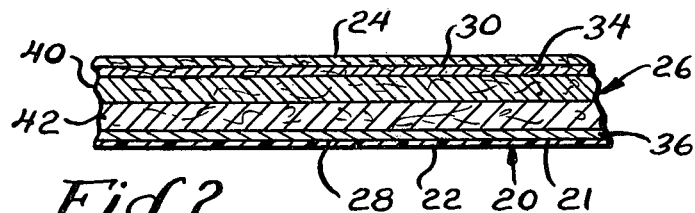
FIG. 2 is a fragmentary sectional view taken substantially as indicated along the line 2—2 of FIG. 1.

Referring now to FIGS. 1 and 2, there is shown an absorbent article or disposable diaper generally designated 20 comprising an absorbent pad assembly 21 having a fluid impervious backing sheet 22, a fluid pervious cover or top sheet 24, and an absorbent pad 26 intermediate the backing and cover sheets 22 and 24, respectively, such that the backing sheet 22 covers the back surface 28 of the absorbent pad 26, while the top sheet 24 covers at least a portion of the front surface 30 of the pad. As shown, the backing sheet 22 may have side margins 32 which are folded over and secured to the sides of the top sheet 24. The diaper may also have a top wadding sheet 34 defining the front surface 30 of the pad 26 adjacent the cover sheet 24, and a back wadding sheet 36 defining the back surface 28 of the pad adjacent the backing sheet 22. The wadding sheets 34 and 36 serve to maintain the structural integrity and prevent balling of the absorbent pad 26 when the pad becomes wet during use.

The diaper 20 may also include a pair of tape fasteners 38 which are used in a known manner to secure the diaper about an infant during placement of the diaper. The diaper 20 may be utilized in its flat condition as shown, or may be folded into a box-pleat configuration, or other suitable configuration, as desired.

As shown, the pad 26 has a first upper layer 40 underlying the top wadding sheet 34 adjacent the cover sheet 24, and a contiguous lower or back second layer 42 located intermediate the first layer 40 and the backing sheet 22, with the wadding sheets 34 and 36 respectively covering outer surfaces of the first and second layers 40 and 42. The layers 40 and 42 of the absorbent pad 26 comprise a mass of loosely formed fibers, such as wood fluff.

A substantial portion of the fibers in the first layer 40 are formed from a mechanically, thermomechanically, or semichemically produced pulp. Also, a substantial portion of the fibers in the second layer 42 are formed from a thermomechanically, semichemically, or chemically produced pulp. If desired, 100% of the fibrous mass in the layers may be formed from the specified pulp, or the mass may comprise a mixture or blend of the specified pulp and other pulps. For convenience of terminology, the mass of fibers formed from a mechanically produced pulp will be termed a mechanical fluff, that formed from a thermomechanically produced pulp will be termed a thermomechanical fluff, that formed from a semichemically produced pulp will be termed a semichemical fluff, and that formed from a chemical pulp will be termed a chemical fluff. In a preferred form the average fibers of the first layer 40 are more hydrophobic relative the average fibers in the second layer 42, or, in other words, the average fibers in the second layer 42 are more hydrophilic relative the average fibers in the first layer 40. As will be discussed below, the average fibers of a mechanical fluff are more hydrophobic than the average fibers of a thermomechanical, semichemical, or chemical fluff. Similarly, the average fibers of a thermomechanical fluff are more hydrophobic than a semichemical or chemical fluff, while the semichemical fluff is more hydrophobic than a chemical fluff. Thus, if a mechanical fluff is utilized in the first layer 40, the second layer 42 is preferably formed from a thermomechanical, semichemical, or chemical fluff. Similarly, if the first layer 40 is formed from a thermomechanical fluff, the second layer is preferably formed from a semichemical or chemical fluff, while if the first layer 40 is formed from a semichemical fluff, the second layer 42 is preferably formed from a chemical fluff. In one form found particularly suitable according to the present invention, the first layer 40 is formed from a thermomechanical fluff, while the second lower layer 42 is formed from a chemical fluff.

As a background to facilitate understanding of the invention, the various pulping processes are discussed below. Pulping itself may be defined for the present purposes as a procedure for rupturing the fibers of wood. The resulting pulp may be used for making paper or in this case absorbent pads. The separated fibers of the pulp are normally formed into pulp board which may be wound into rolls for convenience of handling during shipment and by the user. The rolls are fiberized or comminuted by the user to form a loosely formed fibrous mass which is cut into lengths as absorbent pads for the disposable articles.

Wood itself is primarily composed of cellulose, hemicellulose, and lignin. Lignin is an amorphous polymer of relatively high molecular weight that serves to hold the fibers of wood together. Cellulose is high hydrophilic, while lignin has a significantly reduced affinity for liquid than cellulose and is relatively hydrophobic. Since pulping is concerned with rupturing the bonds between the wood fibers, the middle lamella between the fibers, which is composed mostly of lignin, must be ruptured during the procedure.

Wood logs are transported to the processor, after which bark from the logs may be removed. Generally, the logs are ground into chips, and the chips are used in the pulping procedure to separate fibers in the chips. The fibers are then washed to produce the unbleached pulp, after which the pulp may be bleached to a lighter color pulp. The process differs primarily in the manner the wood is pulped.

The pulping procedures may be categorized as mechanical, chemical, semichemical, and thermomechanical. In mechanical pulping, the logs themselves may be ground by a roughened stone to grind fibers out of the wood. Alternatively, wood chips may be shredded or ground between metal shearing discs in a machine called a refiner. The mechanical pulps produced in this manner are characterized by relatively short fibers due to damage of the fibers during the procedure. Such groundwood processes are relatively efficient in that approximately 95% of the dry weight of the wood is converted into pulp, since materials, such as lignin, are not specially removed from the pulp.

In chemical pulping, the wood chips are cooked in a vessel or digester with chemical reagents to separate the fibers, termed a digesting procedure. During digesting, the pulping reagents degrade and dissolve the lignin to break the bond between the fibers in order that they may be separated. However, the reagents also degrade some of the cellulose and hemicellulose, and the loss of these materials, including lignin, accounts for the relative inefficiency of chemical pulping. Thus, the yield from chemical pulping may range from 40 to 50% of the weight of the wood, with a maximum yield of 55%. Accordingly, chemically produced pulps are significantly higher in cost than mechanical and thermomechanical pulps, the yield of the latter also believed to approach 95%, not to mention the loss of valuable materials during chemical pulping.

The chemically produced pulp is characterized by relatively long fibers which are mostly completely separated. As noted above, the lignin is removed, and the hydrophilic fibers thus produced are susceptible to increased wetting.

The two most common chemical procedures are the sulfite and kraft processes. In the sulfite procedure, an acidic mixture is used as the reagent which is relatively difficult to reclaim, thus posing a risk to the environment when disposed by the processor. In the kraft or sulfate process, the chips are cooked in a solution of sodium hydroxide, sodium carbonate and sodium sulfide. This process results in the emission of gases containing malodorous substances, and is also repugnant to the environment.

In the semichemical process, such as the neutralsulfite process, the wood chips or logs are softened with a chemical, after which the wood is fiberized mechanically, frequently in disc refiners. The fibers produced by the semichemical process retain a greater portion of their natural lignin than those formed from the chemical process, although less than the fibers formed by the mechanical or thermomechanical processes. Also, the yield of the semichemical process is substantially greater than the chemical process, thus reducing the cost of the semichemical pulp.

Finally, in the thermomechanical procedure, wood chips are steamed at an elevated temperature and pressure to soften the lignin. Thus, the binding force between the fibers is greatly lessened through application of heat to permit separation of the fibers. The fibers may be separated by a refiner under pressure or pressure changes.

The thermomechanical procedure produces a large number of substantially undamaged fibers, although some of the fibers remain together. The average fiber length of a thermomechanical pulp in the absorbent pad is in the range of 1.0 mm. to 1.9 mm., although dependent upon the particular species of wood, as in other pulps. For example, a softwood, i.e., the wood of a coniferous, needle-bearing tree, normally results in a longer fiber than a hardwood, i.e., the wood of a boardleaf tree, for a given pulping process. In general, the fiber length of a thermomechanical pulp is greater than that of a mechanical pulp and less than that of a semichemical or chemical pulp for a given species of wood. The greater fiber length of chemical pulps imparts structural integrity and loft to wood fluff, and thus accounts for its widespread use.

Since digestion is not used during the mechanical or thermomechanical procedure, lignin remains of the fibers after being separated, and to a lesser extent on semichemical fibers. Thus, the hydrophilic fibers have relatively hydrophobic or non-hydrophilic surface portions of lignin which reduce wetting of the fibers. Since materials are not removed from the wood by digestion, the yields of the processes are substantially higher than the chemical procedure, and the cost of the corresponding pulps is thus substantially less than chemical pulp, reducing the cost of an article produced from these pulps to the consumer.

Assuming that the nonchemical pulps, or mixture thereof, are formed into pulp board, the hydrogen bonding between the dry fibers is reduced by lignin on the fibers, in contrast to fibers of chemical pulp. Accordingly, the power required to fiberize pulp board containing these pulps is less than that required to perform the same operation on a pulp board of 100% chemical pulp. Again, the reduced pwoer requirements are reflected in a savings of cost to produce the article.

After the pulps have been formed into wood fluff, the absorbent pad comprising the layers 40 and 42 is constructed, as discussed in connection with FIGS. 1 and 2. When the fibers of the more hydrophilic layer 42, such as a chemical fluff, are wetted, the fibers become soft and readily compressible. Thus, when the wetted pad is placed under loads during use, the fibers in the pad layer 42 collapse and the corresponding interfiber spaces in the pad layer 42 become reduced. In contrast, the relatively hydrophobic lignin on fibers in the upper layer 40, such as in mechanical, thermomechanical, or semichemical fluffs, provide the fibers with a greater degree of resiliency than the hydrophilic fibers in chemical fluffs, particularly when the hydrophobic fibers are wetted and placed under loads. Thus, the relatively resilient and hydrophobic fibers of the layer 40 serve to maintain the corresponding interfiber spaces in an open condition, and deter collapse of layer 40 when the pad 27 is wetted and placed under loads.

As a result, the body fluids pass through the cover sheet 24 into the first layer 40 of the pad 26, and after saturation in the localized area where applied to the pad, pass into the second lower pad 42. When wetted and placed under loads, the hydrophilic second layer 42 becomes more absorbent in the wetted and compressed areas relative the first layer 40, and readily draws fluids from the first layer 40 into the second layer 42. Moreover, since the fibers in the second layer 42 collapse to a greater extent than the fibers in the first layer 40 when wetted and placed under loads, the interfiber spacings in the second layer become less than those in the first layer. Thus, the more dense lower layer 42 transmits fluid at a greater rate than the first layer 40, and fluid is spread through the second layer where it is preferentially retained until saturation. Accordingly, the body fluids are absorbed by the second layer 42 from the first layer 40 and are spread through the second layer 42 where they are retained below the first layer 40 at locations spaced from the cover sheet 24. In this manner, the absorbent pad 26 of the present invention minimizes the possibility of back wetting of body fluids from the pad, and maintains the cover sheet which contacts the wearer in a relatively dry condition. In addition, the absorbent pad 26 of the present invention can be made at a reduced cost, due to the relatively low cost of the mechanical, thermomechanical, and semichemical fluffs used in the pad.

Figure 3:
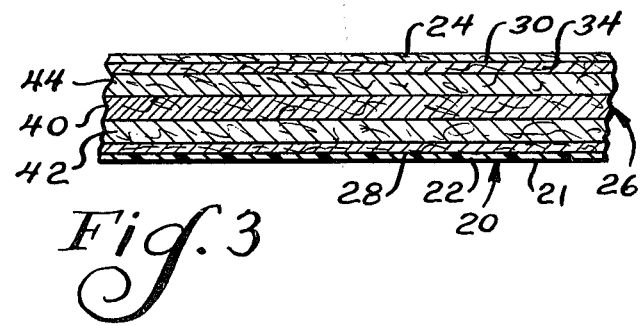
FIG. 3 is a fragmentary sectional view of another embodiment of the article of the present invention.

Another embodiment of the present invention is illustrated in FIG. 3, in which like reference numerals designate like parts. In this embodiment, the pad 26 has a first layer 40 made substantially from a mechanical, thermomechanical, or semichemical fluff, and a lower second layer 42 made substantially from a thermomechanical, semichemical, or chemical fluff. However, in this embodiment, the pad 26 also has a third layer 44 located intermediate the first layer 40 and the cover sheet 24 beneath the top sheet 34, which preferably comprises a chemical fluff. Due to removal of lignin from fibers of the chemical fluff, the chemical fluff in the third layer 44 has a lighter and more usual color for the front portion of the pad. Additionally, since the chemical fibers in the third layer 44 have a greater length than the hydrophobic fibers in the first layer 40, the layer 44 adds structural integrity and loft to the front portion of the pad. In one preferred form, the first layer 40 is made substantially from a thermomechanical fluff, while the second and third layers 42 and 44 are made substantially from a chemical fluff. The pad 26 of FIG. 3 provides for preferential fluid passage from the first layer 40 to second layer 42 for dispersion and retention of the body fluids in the second layer 42, while the third layer 44 provides structural integrity and loft to the front portion of the pad.

The foregoing detailed description is given for clearness of understanding only, and no unnecessary limitations should be understood therefrom, as modifications will be obvious to those skilled in the art.

I claim:

1. A disposable absorbent article of a size for placement against a wearer for capturing body fluids, comprising: a backing sheet of fluid impervious material, a fluid pervious cover sheet, and an absorbent pad positioned intermediate the backing and cover sheets, said pad comprising a plurality of separate layers including a first layer having a mass of fibers substantially formed from a material selected from the group consisting of mechanical pulp, thermomechanical pulp, and semichemical pulp, and a second layer having a mass of fibers substantially formed from a material different from the selected one of the first layer and selected from the group consisting of thermomechanical pulp, semichemical pulp, and chemical pulp, with the average fibers of said first layer being more hydrophobic relative the average fibers of the second layer, and with said second layer being located intermediate the first layer and said backing sheet.

2. The article of claim 1 wherein said pad includes a third layer intermediate the first layer and said cover sheet and having a mass of fibers substantially formed from a chemical pulp.

3. A disposable absorbent article of a size for placement against a wearer for capturing body fluids, comprising: a backing sheet of fluid impervious material, a fluid pervious cover sheet, and an absorbent pad positioned intermediate the backing and cover sheets, said pad comprising a plurality of separate layers including a first layer having a mass of fibers substantially formed from a material selected from the group consisting of mechanical fluff, thermomechanical fluff, and semichemical fluff, and a second layer having a mass of fibers substantially formed from a material different from the selected one of the first layer and selected from the group consisting of thermomechanical fluff, semichemical fluff, and chemical fluff, with the average fibers of the second layer being more hydrophilic relative the average fibers of the first layer, and with said second layer being located intermediate the first layer and said backing sheet.

4. The article of claim 3 wherein said first layer is located adjacent said cover sheet and said second layer is located adjacent said backing sheet.

5. The article of claim 4 including a top wadding sheet covering a front surface of the first layer, and a back wadding sheet covering a back surface of the second layer.

6. The article of claim 4 wherein said first and second layers are contiguous.

7. A disposable absorbent article of a size for placement against a wearer for capturing body fluids, comprising: a backing sheet of fluid impervious material, a fluid pervious cover sheet, and an absorbent pad positioned intermediate the backing and cover sheets, said pad comprising a plurality of separate layers including a first layer having a mass of fibers substantially formed from a mechanical fluff, and a second layer having a mass of fibers substantially formed from a material selected from the group consisting of thermomechanical fluff, semichemical fluff, and chemical fluff, with said second layer being located intermediate the first layer and said backing sheet.

8. A disposable absorbent article of a size for placement against a wearer for capturing body fluids, comprising: a backing sheet of fluid impervious material, a fluid pervious cover sheet, and an absorbent pad positioned intermediate the backing and cover sheets, said pad comprising a plurality of separate layers including a first layer having a mass of fibers substantially formed from a thermomechanical fluff, and a second layer having a mass of fibers substantially formed from a material selected from the group consisting of semichemical fluff, and chemical fluff, with said second ayer being located intermediate the first layer and said backing sheet.

9. A disposable absorbent article of a size for placement against a wearer for capturing body fluids, comprising: a backing sheet of fluid impervious material, a fluid pervious cover sheet, and an absorbent pad positioned intermediate the backing and cover sheets, said pad comprising a plurality of separate layers including a first layer having a mass of fibers substantially formed from a semichemical fluff, and a second layer having a mass of fibers substantially formed from a chemical fluff, with said second layer being located intermediate the first layer and said backing sheet.

* * * * *

UNITED STATES PATENT AND TRADEMARK OFFICE
CERTIFICATE OF CORRECTION

PATENT NO. : 4,047,531
DATED : September 13, 1977
INVENTOR(S) : Hamzeh Karami

It is certified that error appears in the above—identified patent and that said Letters Patent are hereby corrected as shown below:

In column 1, line 16, "pump" should be -- pulp -- .

In column 5, line 55, "of" should be -- on -- .

In column 8, line 37, "ayer" should be -- layer -- .

Signed and Sealed this

Twenty-first Day of February 1978

[SEAL]

*Attest:*

RUTH C. MASON
*Attesting Officer*

LUTRELLE F. PARKER
*Acting Commissioner of Patents and Trademarks*